United States Patent

Kusens

(10) Patent No.: US 10,614,564 B2
(45) Date of Patent: *Apr. 7, 2020

(54) METHOD TO DETERMINE IMPAIRED ABILITY TO OPERATE A MOTOR VEHICLE

(71) Applicant: COLLATERAL OPPORTUNITIES, LLC, Wilmington, DE (US)

(72) Inventor: Michael Kusens, Cooper City, FL (US)

(73) Assignee: COLLATERAL OPPORTUNITIES, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 16/119,486

(22) Filed: Aug. 31, 2018

(65) Prior Publication Data

US 2019/0019283 A1 Jan. 17, 2019

Related U.S. Application Data

(63) Continuation of application No. 15/915,565, filed on Mar. 8, 2018, now Pat. No. 10,096,101, which is a
(Continued)

(51) Int. Cl.
*G06T 7/00* (2017.01)
*H04N 13/204* (2018.01)
*G06K 9/00* (2006.01)
*G06T 7/285* (2017.01)
*G16H 50/30* (2018.01)
(Continued)

(52) U.S. Cl.
CPC ........ *G06T 7/0002* (2013.01); *G06K 9/00845* (2013.01); *G06T 7/0014* (2013.01); *G06T 7/20* (2013.01); *G06T 7/246* (2017.01); *G06T 7/285* (2017.01); *G06T 7/292* (2017.01); *G06T 7/73* (2017.01); *G16H 50/30* (2018.01); *H04N 13/204* (2018.05); *G06T 2207/10021* (2013.01); *G06T 2207/30004* (2013.01); *G06T 2207/30196* (2013.01)

(58) Field of Classification Search
CPC combination set(s) only.
See application file for complete search history.

(56) References Cited

U.S. PATENT DOCUMENTS 7,087,015 B1 * 8/2006 Comrie ................ G06F 19/325
                                                                                              600/300
8,950,864 B1 * 2/2015 Massengill .......... A61B 5/4064
                                                                                              351/209

(Continued)

*Primary Examiner* — Janese Duley
(74) *Attorney, Agent, or Firm* — Daniel S. Polley, P.A.

(57) ABSTRACT

A method and system for determining if an individual is impaired. In one embodiment, physical and cognitive testing of the individual are conducted in the field or at the scene of an event. The test results are compared to previously stored baseline test results taken for the specific individual while the individual is known to be in an unimpaired state or condition. The current test results are electronically compared to the baseline test results and if the results differ or deviate beyond a predetermined level or amount the individual is considered to be impaired. If no baseline test results exist for the specific individual, the current test results can alternatively be compared to previously determined or known scientifically accepted or minimums for the specific tests given to the individual.

12 Claims, 4 Drawing Sheets

Related U.S. Application Data continuation of application No. 14/670,987, filed on Mar. 27, 2015, now Pat. No. 9,916,649, which is a continuation-in-part of application No. 14/662,215, filed on Mar. 18, 2015, now abandoned.

(60) Provisional application No. 61/954,913, filed on Mar. 18, 2014.

(51) Int. Cl.
  *G06T 7/20* (2017.01)
  *G06T 7/292* (2017.01)
  *G06T 7/73* (2017.01)
  *G06T 7/246* (2017.01)

(56) References Cited

U.S. PATENT DOCUMENTS

| | | | | |
|---|---|---|---|---|
| 2008/0309616 A1* | 12/2008 | Massengill | ............ | A61B 3/113 |
| | | | | 345/156 |
| 2014/0142439 A1* | 5/2014 | French | ................ | A61B 5/4088 |
| | | | | 600/483 |
| 2015/0096002 A1* | 4/2015 | Shuart | .................... | G06F 21/32 |
| | | | | 726/7 |

* cited by examiner

METHOD TO DETERMINE IMPAIRED ABILITY TO OPERATE A MOTOR VEHICLE

This application is a continuation of U.S. application Ser. No. 15/915,565, filed Mar. 8, 2018, which is a continuation of U.S. application Ser. No. 14/670,987, filed Mar. 27, 2015, now U.S. Pat. No. 9,916,649, which is a continuation-in-part of U.S. application Ser. No. 14/662,215, filed Mar. 18, 2015, now abandoned, which claims the benefit of and priority to U.S. Provisional Patent Application Ser. No. 61/954,913, filed Mar. 18, 2014. All of the above applications are incorporated by reference in their entireties for all purposes.

1. FIELD OF THE DISCLOSURE

The present disclosure is directed to field test to determine if an individual is impaired.

2. BACKGROUND

In the current environment, over 1.2 million drivers in the United States are arrested each year for driving under the influence according to statistics released by the Federal Bureau of Investigations. Several factors are utilized by law enforcement to determine impairment by a driver including the results of field sobriety and chemical tests, many of which are subjective in nature. With regard to field sobriety tests, the National Highway Traffic Safety Administration (NHTSA) has developed a model system for measuring sobriety called the Standardized Field Sobriety Test (SFST), which includes three tests. These tests are designed to determine the likelihood of a driver having blood alcohol concentrations greater then a specific level. However, according to published studies by the NHTSA, the effectiveness of any given single test is between 79% and 88% in making such a determination with a combined accuracy of 91%.

There are several pitfalls with this method of testing though. First, it does not actually attempt to measure the level of impairment or driving ability but rather just the level of alcohol content in a person's system. Secondly, there are numerous other substances that can cause impairment such as prescription medications and recreational drugs. Thirdly, none of these tests measure an individual's actual ability to operate a motor vehicle. Fourthly, the tests are subjective in nature and require an individual to make a determination based on what they observe. Lastly, none of these tests are done with any basis for comparison to the individuals' ordinary abilities without the influence of alcohol, prescription medications or recreational drugs nor do they take into consideration any medical conditions, injuries or other factors, which may affect the individuals' ability to perform these tests.

The present disclosure is directed to addressing the above-identified problems with current testing for driving impairment.

SUMMARY OF THE DISCLOSURE

Several embodiments for a novel system and method are provided that allow individuals, law enforcement personnel, or any other authority to obtain and objectively measure the level of impairment on an individual basis, taking into consideration any medical conditions, injuries, mental limitations or other factors effecting an individuals ability to operate a motor vehicle.

The following non-limiting definitions are provided as an aid in understanding the disclosed novel system and method:

| | |
|---|---|
| 3D Camera, Eye Tracking, Motion and Sound Sensor | An electronic device that contains one or more cameras capable of identifying individual objects, people and motion regardless of lighting conditions as well as one or more microphones to detect audio. The cameras can record video and can utilize technologies including but not limited to color RGB, CMOS sensors, infrared projectors and RF-modulated light. They may also contain microprocessors and image sensors to detect and process information both sent out and received by the various cameras.<br>The electronic device calculates if there has been a change in location of the person or object of interest over a period of time. As a non-limiting example, a person's right knee can be at time T1 located at coordinates (x1, y1, z1) in a picture frame taken by the camera (i.e. picture frame at time T1 from the video recorded by the camera). At time T2 the right knee is capture by the picture frame of the video taken by the camera at coordinates (x2, y2, z2) (i.e. picture frame at time T2 from the video recorded by the camera). Based on this information, motion, speed and direction can be derived utilizing the elapsed time and comparing the two 3D coordinates over the elapsed time. As opposed to conventional motion sensors, which use captured motion to control a camera, the 3D Motion and Sound Sensor used with the method and system, uses the camera in order to compute the motion.<br>While the testing is being conducted (i.e. current "in field" testing or baseline testing), the camera is preferably continuously on and recording the actions of the individual, regardless of whether the person of interest is moving or not.<br>The camera does not require any triggering event to cause the camera to begin recording video and/or 3D depth data or transmitting video and/or 3D depth data to the other components of the system for analysis or storage. Preferably, the camera will be turned on by the user prior to the beginning of the testing and will be turned off after the testing is completed.<br>Preferably, the camera portion records, captures and/or streams video and/or 3D depth data. As video is technically made up of individual picture frame (i.e. 30 frames per second of video), the above reference to picture frames is referring to frames of video.<br>The camera can also be configured or designed to also take still pictures (i.e. for taking a picture of the individual in the field/on the |

| | |
|---|---|
| | scene to show injuries, bruises, etc. received from an associated accident, etc.).<br>Additionally, the electronic device can also be capable of identifying and tracking the movement of an individual's eye. A camera focuses on one or both eyes and records their movement as the individual looks at some kind of stimulus. The center of the pupil and infrared/near-infrared non-collimated light are used to create corneal reflections (CR). The vector between the pupil center and the corneal reflections can be used to compute the point of regard on surface or the gaze direction. Two general types of eye tracking techniques can be used: bright-pupil and dark-pupil. Bright-pupil has the illumination source coaxial with the optical path, causing the eye to act as a retroreflector as the light reflects off the retina creating a bright pupil effect similar to red eye. In dark-pupil, If the illumination source is offset from the optical path, then the pupil appears dark because the retroreflection from the retina is directed away from the camera.<br>The 3D Motion and Sound Sensor can be preferably located in a law enforcement vehicle, attached to, embedded in or otherwise in communication with an information input and display device, which is described below. |
| Information Input and Display Device | An electronic device that allows the display and capture of electronic data including but not limited to text, pictures, video and sound to the eyes and ears of the individual holding, viewing and/or wearing said device. Examples of such a device include but are not limited to phones, tablets, laptop computers and augmented vision headwear (Google Glass or similar). The Information Input and Display Device may be integrated with the 3D Camera, Eye Tracking, Motion and Sound Sensor or they can be separate electronic devices. |
| Physical and Cognitive Ability Testing System | An electronic system and software installed or embedded in an electronic device including but not limited to a computer, tablet, server, cell phone, smart phone, microprocessor, microcontroller or other such electronic device designed to test and record the physical and cognitive abilities of a individual that impact said individuals' ability to operate a vehicle and stores such information in a database. |
| Physical and Cognitive Ability Testing System Database | An electronic database that stores physical and cognitive testing results provided, recorded or otherwise obtained by the physical and cognitive ability testing system. |
| Physical and Cognitive Ability Baseline Database | An electronic database that stores physical and cognitive testing results commonly accepted in the scientific community and industry. |

DETAILED DESCRIPTION

Figure 1:
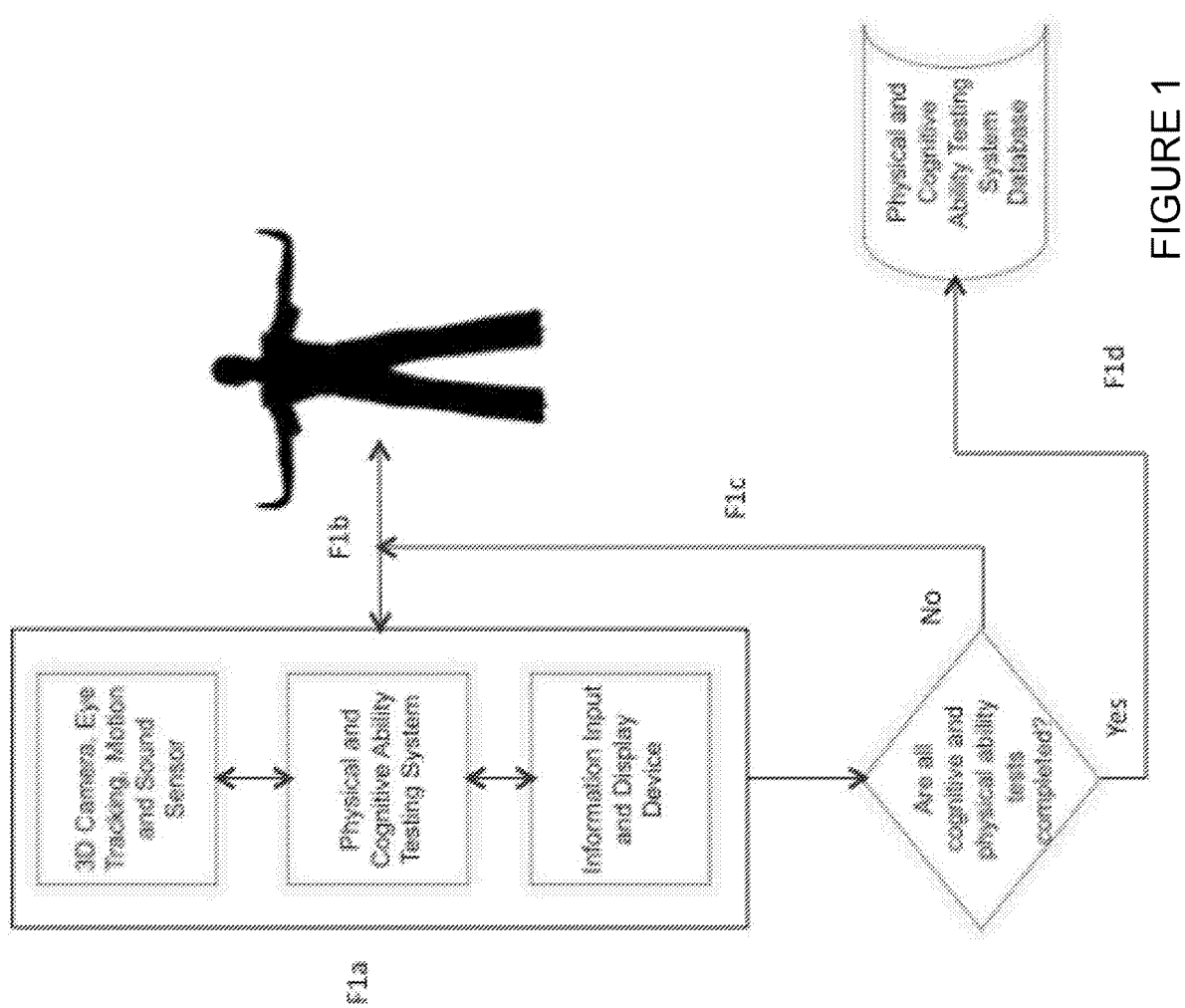
FIG. 1 illustrates a block diagram and process flow for creating a baseline testing of an individual's normal physical and cognitive abilities.

FIG. 1 illustrates a block diagram and general steps performed in one embodiment for baseline testing of an individual's physical and cognitive abilities under to establish baseline results for the individual under normal conditions (i.e. no alcohol, no medications, and/or no drugs, etc. in the individual's body that could affect his or her physical and/or cognitive abilities). The achieved baseline levels for the individual are then preferably stored for later use to compare to subsequent "on the scene" test results for the same individual based on an "in the field" event (i.e. pulled over by a police officer in view of the individual weaving while driving, individual was responsible for a car accident, pulled over for excessive speeding, inc.).

At step F1a, a 3D camera, eye tracking, motion and sound sensor is attached to, integrated or otherwise in communication with an information input and display device which also contains the physical and cognitive ability testing system software. Preferably, the 3D camera records video and 3D depth data for the individual while he or she proceeds or performs through the various tests making up the baseline test for the specific individual's normal physical and cognitive abilities.

At step F1b, the individual interacts with the physical and cognitive ability testing system through the information input and display device while also incorporating information generated by the 3D camera, eye tracking, motion and sound sensor, such as information determined from the recorded video. The Physical and Cognitive Ability testing system utilizes a series of questions, activities and movements to determine the level of cognitive ability, reaction time, and physical capabilities/limitations of the individual. The system can be utilized with one or many of the available tests and is not required to have results for all tests in order to function.

At step F1c, the Physical and Cognitive Ability Testing System continues through a series of tests until the last of the test is completed or a sufficient number of tests have been completed. There is no limitation as to the minimum number of tests that have to be completed, and the described system and method can properly function with a single test being completed.

At step F1*d*, where a single or multiple tests are to be performed, once the (all) test(s) is(are) completed, the results of the test(s) are stored in a database along with identifying information for the individual including but not limited to name, birth date, address and drivers license number.

Figure 2:
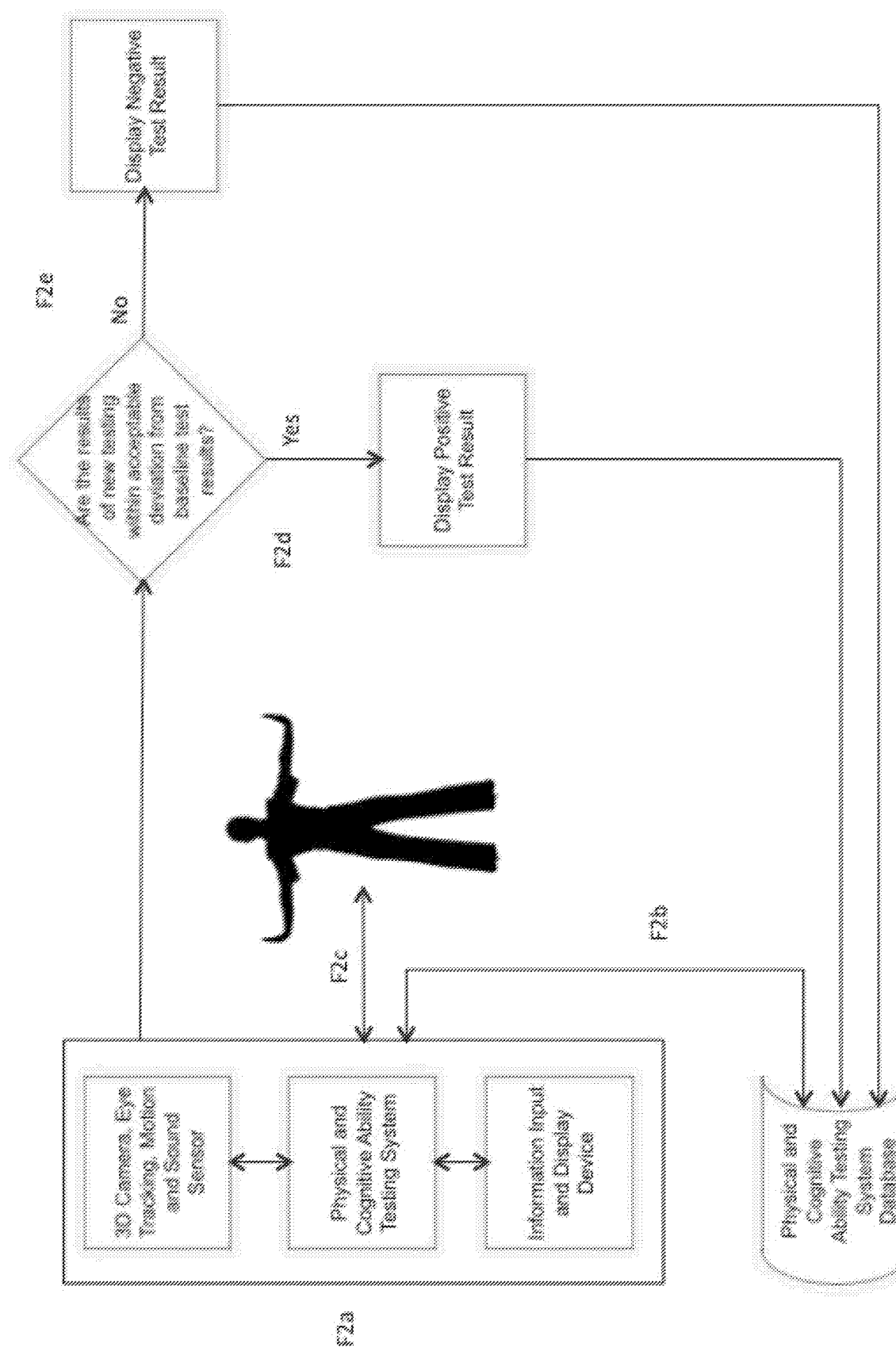
FIG. 2 illustrates a block diagram and process flow for comparing the baseline testing results of FIG. 1 to current/new "in the field" test results for the individual.

FIG. 2 illustrates a block diagram and flow steps for comparing the results of current test (i.e. performed in the field, at the scene of an event, back at the police station, etc.) to the baseline test results obtained from the steps described in FIG. 1 for the individual. The method and system in FIG. 2 determines whether an individual's current test results are within an acceptable standard deviation from the known baseline results for that specific individual.

At step F2*a*, a 3D camera, eye tracking, motion and sound sensor is attached to, integrated or otherwise in communication with an information input and display device which also contains the physical and cognitive ability testing system software. At step F2*b*, the Physical and Cognitive Ability Testing System queries the database to retrieve prior baseline test results for a given specific individual.

At step F2*c*, an individual interacts with the physical and cognitive ability testing system through the information input and display device while also incorporating information generated by the 3D camera, eye tracking, motion and sound sensor, such as, but not limited to, through information obtained from the video recording made by the 3D camera. The Physical and Cognitive Ability testing system utilizes a series of questions, activities and movements to determine the level of cognitive ability, reaction time, and physical capabilities/limitations of the individual. The system can be utilized with one or many of the available tests and is not required to have results for all tests in order to function.

At step F2*d*, the results of the current tests are compared against the individuals own baseline tests, which were preferably taken while the individual was sober or otherwise unimpaired. If the current test results are within an acceptable statistical standard deviation from the baseline results, a positive test result is displayed on the Information Input and Display device and a notation is made in the database recording such result along with storing the current individual test results for the individual.

At step F2*e*, if the current test results are not within an acceptable statistical standard deviation from the baseline result, a negative result is displayed on the Information Input and Display Device indicating possible impairment for the individual and a notation is made in the database recording such result along with storing the current individual test results for the individual. The current test results do not replace the baseline results for an individual but rather are added as a second data record to be used in future testing and analysis.

A negative result can be used by, or be considered a factor by, an attending officer when such officer decides whether or not to charge, arrest, warn, fine, etc. the individual for driving while under the influence, while intoxicated, drunk driving, etc.

Figure 3:
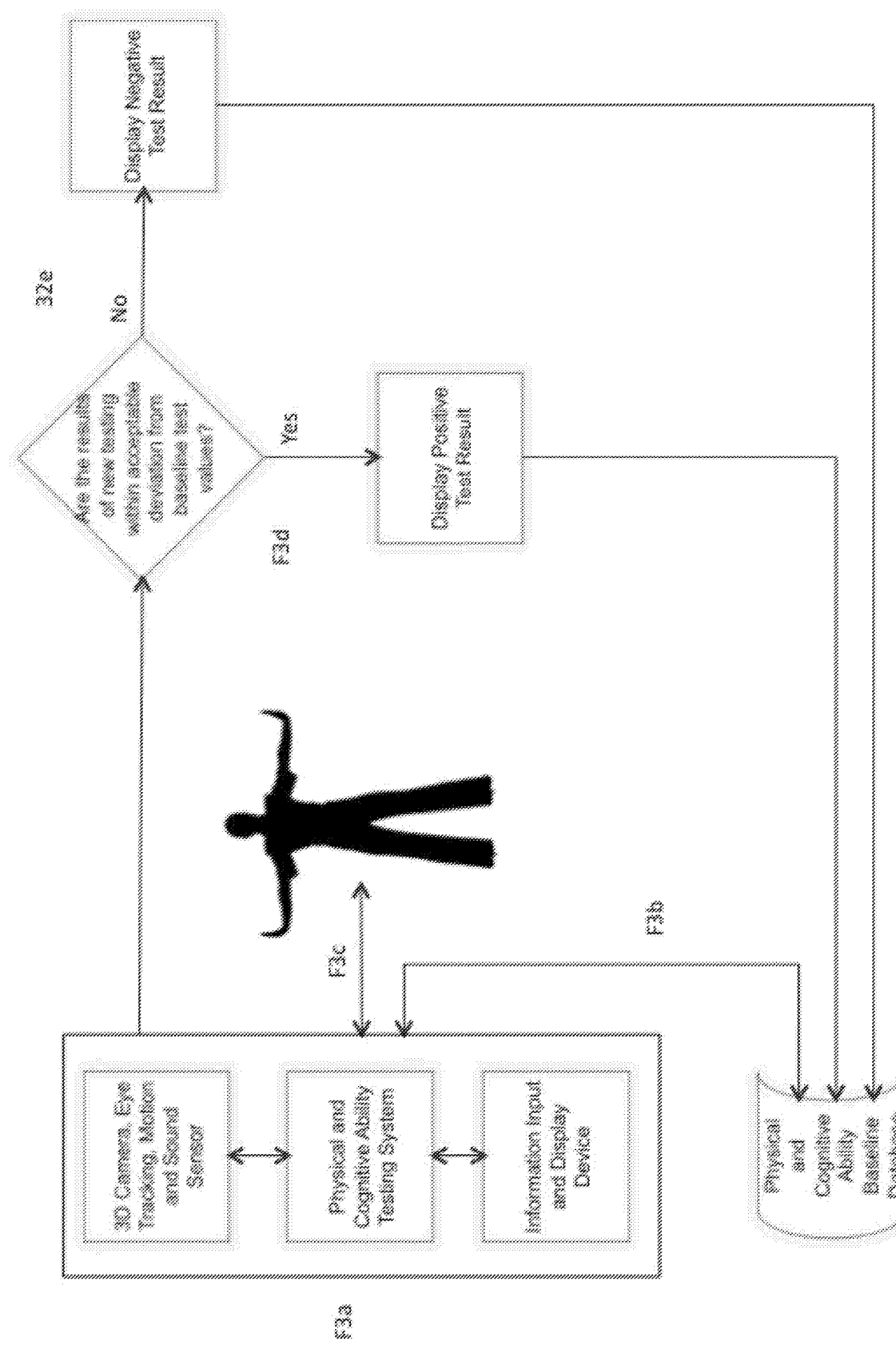
FIG. 3 illustrates a block diagram and process flow for comparison a stored scientifically accepted baseline results to current/new "in the field" test results for the individual.

FIG. 3 illustrates a block diagram and flow steps for comparing the results of current test (i.e. performed in the field, at the scene of an event, back at the police station, etc.) to previously established scientifically accepted baseline results for the specific tests given to the individual during the current test. The method and system in FIG. 3 determines whether an individual's current test results are within an acceptable standard deviation from the known scientifically accepted baseline results for the general population.

At step F3*a*, a 3D camera, eye tracking, motion and sound sensor is attached to, integrated or otherwise in communication with an information input and display device which also contains the physical and cognitive ability testing system software. At step F3*b*, the Physical and Cognitive Ability Testing System queries the database to retrieve the baseline results derived from scientifically accepted minimum capabilities for each test.

At step F3*c*, an individual interacts with the physical and cognitive ability testing system through the information input and display device while also incorporating information generated by the 3D camera, eye tracking, motion and sound sensor, such as, but not limited to, through information obtained from the video recording made by the 3D camera. The Physical and Cognitive Ability testing system utilizes a series of questions, activities and movements to determine the level of cognitive ability, reaction time, and physical capabilities/limitations of the individual. The system can be utilized with one or many of the available tests and is not required to have results for all tests in order to function.

At step F3*d*, the results of the current tests for a given individual are compared against the baseline results derived from scientifically accepted minimum capabilities for each test. If the current test results are within an acceptable statistical standard deviation from the baseline results, a positive test result is displayed on the Information Input and Display device and a notation is made in the database recording such result along with storing the current individual test results for the individual.

At step F3*e*, if the current test results are not within an acceptable statistical standard deviation from the baseline result, a negative result is displayed on the Information Input and Display Device indicating possible impairment for the individual and a notation is made in the database recording such result along with storing the current individual test results for the individual. The current test results do not replace the scientifically derived baseline results but rather are added as a different data record to be used in future testing and analysis.

Similar to the embodiment described in FIG. 2, a negative result can be used by, or be considered a factor by, an attending officer when such officer decides whether or not to charge, arrest, warn, fine, etc. the individual for driving while under the influence, while intoxicated, drunk driving, etc.

Figure 4:
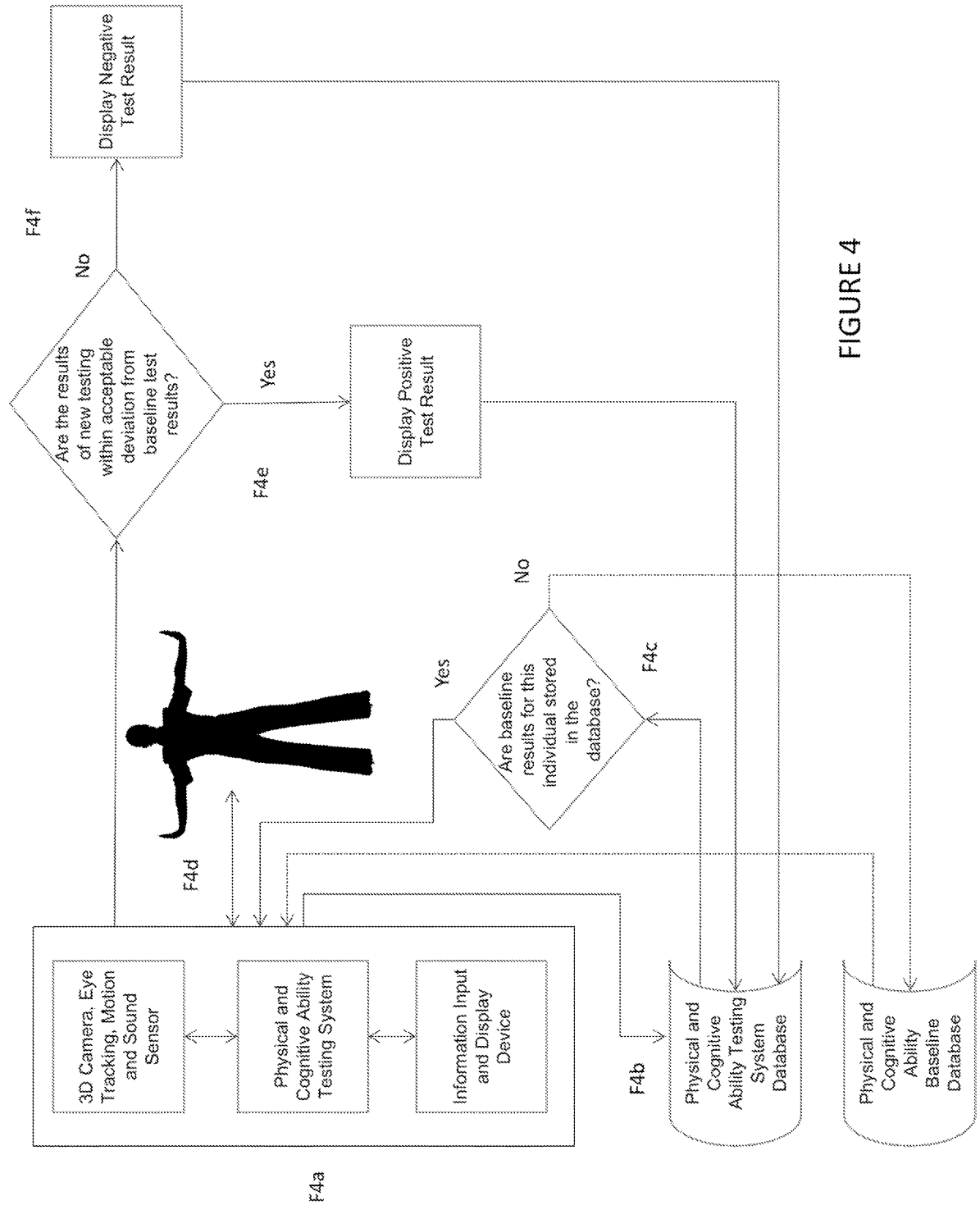
FIG. 4 illustrates a block diagram and process flow for comparing the baseline testing results of FIG. 1 or scientifically accepted baseline results to an individual's current/new "in the field" test results.

FIG. 4 illustrates a block diagram and flow steps for comparing the results of current test (i.e. performed in the field, at the scene of an event, back at the police station, etc.) to the baseline test results obtained from steps of FIG. 1 for the individual, and if there are no baseline test results for the specific individual, than alternatively to the previously established scientifically accepted baseline results for the specific tests given to the individual during the current test. The method and system in FIG. 4 determines whether an individual's current test results are within an acceptable standard deviation from the baseline test results for the specific individual or from known scientifically accepted baseline results for the general population. The method and system of FIG. 4 determines whether an individual's current test results are within an acceptable standard deviation from known baseline results for that specific individual or in the absence of baseline results for that specific individual to scientifically accepted baseline results.

At step F4*a*, a 3D camera, eye tracking, motion and sound sensor is attached to, integrated or otherwise in communication with an information input and display device which also contains the physical and cognitive ability testing system software. At step F4b, the Physical and Cognitive Ability Testing System queries the database to determine if prior testing results exist for the individual.

At step F4c, if a record is found, that information is retrieved by the Physical and Cognitive Ability Testing System. If no record is found, a default, previously stored baseline result for each test is retrieved. The default baseline results are derived from scientifically accepted minimum capabilities necessary to properly operate a motor vehicle.

At step F4d, an individual interacts with the physical and cognitive ability testing system through the information input and display device while also incorporating information generated by the 3D camera, eye tracking, motion and sound sensor, such as, but not limited to, through information obtained from the video recording made by the 3D camera. The Physical and Cognitive Ability testing system utilizes a series of questions, activities and movements to determine the level of cognitive ability, reaction time, and physical capabilities/limitations of the individual. The system can be utilized with one or many of the available tests and is not required to have results for all tests in order to function.

At step F4e, the results of the current tests for a given individual are compared against either the baseline results for that individual or derived from scientifically accepted minimum capabilities for each test. If the current test results are within an acceptable statistical standard deviation from the baseline results, a positive test result is displayed on the Information Input and Display device and a notation is made in the database recording such result along with storing the current individual test results for the individual.

At step F4f, if the current test results are not within an acceptable statistical standard deviation from the baseline result used in F4e, a negative result is displayed on the Information Input and Display Device indicating possible impairment for the individual and a notation is made in the database recording such result along with storing the current individual test results for the individual. The current test results do not replace the existing baseline results for that individual or scientifically derived baseline results but rather are added as a different data record to be used in future testing and analysis.

Similar to the other described embodiments, a negative result can be used by, or be considered a factor by, an attending officer when such officer decides whether or not to charge, arrest, warn, fine, etc. the individual for driving while under the influence, while intoxicated, drunk driving, etc.

The camera and sound sensor can also record the individual's speech and test such speech for slurring, against recordings of the specific individual when sober or against other scientifically accepted records of unimpaired speech.

For all of the above-described embodiments which use specific baseline results for the individual, where an event has occurred to the individual subsequent to the recording of his or her baseline results (i.e. injury to one or more of the individual's limbs, head injury, etc.), updated baseline results can be recorded for the individual, which can be added to the individual's stored results or stored or recorded over the individual previous results prior to the event. In all embodiments, the system can also be used to store and note any specific information for the individual which could be considered relevant to law enforcement personnel such as, but not limited to, medications taken by the individual or known illnesses suffered by the individual.

The system preferably uses several components, which can include the non-limiting following components:
1. 3D Camera, Eye Tracking, Motion and Sound Sensor
2. Information Input and Display Device
3. Physical and Cognitive Ability Testing System
4. Physical and Cognitive Ability Testing System Database
5. Physical and Cognitive Ability Baseline Database
6. Scientifically Accepted and Validated Baseline Test Results.

The various components can be in communication with each other through any known wired or wireless technology.

The utilization of a computerized physical and cognitive ability testing system and database to determine an individuals impairment at a given point in time as compared to previously known capabilities for the individual or scientifically accepted minimum capabilities will provide significant administrative, clinical, and financial benefit to law enforcement, legal systems, drivers license agencies and motor vehicle operators alike, including the following, non-limiting public benefits:
1. Objective and recorded testing for potential motor vehicle driver impairment
2. Individualized impairment testing based on normal capabilities of the individual factoring preexisting physical, medical and cognitive limitations and capabilities or in the alternative testing compared to scientifically accepted baseline results.
3. Reduction in false accusation of motor vehicle operator impairment
4. Reduction is legal system costs due to false accusations of motor vehicle impairment Any computer/server/electronic database system (collectively "Computer System") capable of being programmed with the specific steps of the present invention can be used and is considered within the scope of the disclosure. Once programmed such Computer System can preferably be considered a special purpose computer limited to the use of two or more of the above particularly described combination of steps (programmed instructions) performing two or more of the above particularly described combination of functions.

All components of the present disclosure system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. currently known and/or later developed can also be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the disclosure has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A method for determining if a specific individual is currently impaired or unimpaired, the method comprising the steps of:
   (a) obtaining video of current physical or cognitive abilities of the specific individual performing one or more physical or cognitive test for use in determining whether the specific individual is currently impaired;
   (b) electronically forwarding the video to a Physical and Cognitive Ability Testing System;
   (c) obtaining previously stored baseline test results for the one or more physical or cognitive tests by the Physical and Cognitive Ability Testing System from an electronic database in communication with the Physical and Cognitive Ability Testing System;
   (d) comparing the obtained current test results with the previously stored baseline test results by the physical and cognitive ability testing system;
   (e) based on the comparison in step (d) determining by the physical and cognitive ability testing system if the current test results deviate from the baseline test results beyond a predefined deviation level; and
   (f) if the determination in step (e) determines that the current test results deviate beyond the predefined deviation level indicating that the specific individual may be impaired or if the determination in step (e) determines that the current test results do not deviate beyond the predefined deviation level indicating that the specific individual does not appear to be impaired;
   wherein the previously obtained baseline test results are obtained by the following steps:
   (i) capturing video of a specific unimpaired individual with a 3D video camera while the individual performs one or more physical or cognitive test used for determining whether the individual is driving while impaired by law enforcement;
   (ii) forwarding the captured video to the Physical and Cognitive Ability Testing System which is in electronic communication with the 3D video camera;
   (iii) processing information from the captured video by the Physical and Cognitive Ability Testing System to obtain electronic baseline results information for the individual representing the physical and cognitive abilities of the individual in the unimpaired state when performing the one or more physical or cognitive test used for determining whether the individual is driving while impaired; and
   (iv) storing the electronic baseline results information in the database.

2. The method for determining of claim 1 wherein the previously obtained baseline test results are previously stored minimum capability results.

3. The method of claim 1 further comprising a step of adding electronic identifying information for the specific individual to the current test results and storing the current test results along with the identifying information in the electronic database.

4. The method of claim 1 further comprising a step of pulling the specific individual over by a law enforcement officer prior to step (a).

5. A method for determining if a specific individual is currently impaired or unimpaired, the method comprising the steps of:
   (a) obtaining video of current physical and cognitive abilities of the specific individual performing one or more physical or cognitive test for use in determining whether the specific individual is currently impaired while performing a specific activity;
   (b) electronically forwarding the video to a Physical and Cognitive Ability Testing System;
   (c) determining if there are previously obtained baseline test results stored in an electronic database of the physical and cognitive abilities of the specific individual performing the one or more tests while the specific individual is in an unimpaired state or condition by the Physical and Cognitive Ability Testing System and (i) if yes, receiving the stored baseline test results by the Physical and Cognitive Ability Testing System and comparing obtained current test results with the baseline test results by the Physical and Cognitive Ability Testing System, or (ii) if no, receiving known minimum capability results for the one or more tests by the Physical and Cognitive Ability Testing System and comparing the obtained current test results with the known minimum capability results;
   (d) determining by the physical and cognitive ability testing system if current test results deviate from the baseline test results or the known minimum capability results beyond a predefined deviation level; and
   (e) if the determination in step (d) determines that the current test results deviate beyond the predefined deviation level indicating that the specific individual may be impaired or if the determination in step (d) determines that the current test results do not deviate beyond the predefined deviation level indicating that the specific individual does not appear to be impaired;
   wherein the previously obtained baseline test results are obtained by the following steps:
   (i) capturing video of a specific unimpaired individual with a 3D video camera while the individual performs one or more physical or cognitive test used for determining whether an individual is driving while impaired by law enforcement;
   (ii) forwarding the captured video to the Physical and Cognitive Ability Testing System which is in electronic communication with the 3D video camera;
   (iii) processing information from the captured video by the Physical and Cognitive Ability Testing System to obtain electronic baseline results information for the individual representing the physical and cognitive abilities of the individual in an unimpaired state when performing the one or more physical or cognitive test used for determining whether an individual is driving while impaired by law enforcement; and
   (iv) storing the electronic baseline results information in the database.

6. The method for determining of claim 5 further comprising a step of storing the current test results in the electronic database.

7. The method for determining of claim 5 wherein the known minimum capability results are stored in the electronic database.

8. The method of claim 5 further comprising a step of adding electronic identifying information for the specific individual to the current test results and storing the current test results along with the identifying information in the electronic database.

9. The method of claim 5 further comprising the step of pulling the specific individual over by a law enforcement officer prior to step (a).

10. The method of claim 5 wherein the specific activity is driving a vehicle by the specific individual.

11. The method for determining of claim 1 wherein the previously obtained baseline test results are baseline test results of the physical or cognitive abilities of the specific individual while the specific individual is in an unimpaired state or condition.

12. The method for determining of claim 5 wherein the previously obtained baseline test results are baseline test results of the physical and cognitive abilities of the specific individual while the specific individual is in an unimpaired state or condition.

* * * * *